United States Patent [19]

Matsuyama et al.

[11] Patent Number: 5,312,757
[45] Date of Patent: May 17, 1994

[54] SAMPLE DISTRIBUTING METHOD

[75] Inventors: Sinya Matsuyama, Tokyo; Takashi Yamada, Sagamihara, both of Japan

[73] Assignee: Olympus Optical Co., Ltd., Tokyo, Japan

[21] Appl. No.: 871,952

[22] Filed: Apr. 21, 1992

[30] Foreign Application Priority Data

May 2, 1991 [JP] Japan .................. 3-100701
May 2, 1991 [JP] Japan .................. 3-100702
May 2, 1991 [JP] Japan .................. 3-100783

[51] Int. Cl.$^5$ .................. B01L 3/02; G01N 35/02
[52] U.S. Cl. .................. 436/54; 436/49; 436/50; 436/52; 436/53; 436/55; 436/180; 422/65; 422/81; 422/82; 422/100; 422/105; 73/864.11
[58] Field of Search .................. 436/52, 53, 54, 43, 436/174, 180, 50, 49, 55; 422/63, 65, 81, 82, 99, 100, 105; 73/864.11, 864.14, 864.18, 864.22, 864.35

[56] References Cited

U.S. PATENT DOCUMENTS

| | | | |
|---|---|---|---|
| 3,754,444 | 8/1973 | Ure et al. | 73/864.22 |
| 3,972,683 | 8/1976 | Lape | 23/259 |
| 4,130,394 | 12/1978 | Negersmith | 23/230 R |
| 4,457,184 | 7/1984 | Shiono | 73/864.11 |
| 4,517,850 | 5/1985 | Wiseman et al. | 73/864.21 |
| 4,555,957 | 12/1985 | Frankel et al. | 73/864.14 |
| 4,794,085 | 12/1988 | Jessop et al. | 436/54 |
| 4,863,695 | 9/1989 | Fullemann | 422/100 |
| 5,013,529 | 5/1991 | Itoh | 422/100 |
| 5,045,286 | 9/1991 | Kitajima et al. | 422/100 |
| 5,143,849 | 9/1992 | Barry et al. | 436/50 |

FOREIGN PATENT DOCUMENTS

| | | |
|---|---|---|
| 0185330 | 5/1986 | European Pat. Off. . |
| 2558672 | 12/1977 | Fed. Rep. of Germany . |
| 3024823 | 1/1981 | Fed. Rep. of Germany . |
| 3733098 | 4/1988 | Fed. Rep. of Germany . |
| 3839896A1 | 6/1989 | Fed. Rep. of Germany . |
| 282082 | 8/1990 | Fed. Rep. of Germany . |
| 4011584A1 | 10/1990 | Fed. Rep. of Germany . |

Primary Examiner—James C. Housel
Assistant Examiner—Long V. Le
Attorney, Agent, or Firm—Frishauf, Holtz, Goodman & Woodward

[57] ABSTRACT

A syringe is depressurized to suck a slight amount of air into the tip portion of a probe of a probe assembly, forming an air layer. Then, the syringe is depressurized again to suck into the probe assembly a sample to be discharged into a reaction container. Accordingly, the target sample to be discharged, the air layer and extruding water are placed into the probe assembly in the named order from the tip portion of the probe.

5 Claims, 2 Drawing Sheets

SAMPLE DISTRIBUTING METHOD

BACKGROUND OF THE INVENTION
1. Field of the Invention

The present invention relates to a sample distributing method for measuring the steady quantity of the concentrations of chemical components of a sample, such as blood cells, blood plasma, blood serum or urine.

2. Description of the Related Art

Conventionally, this type of method is applied to a sample distributor which test a body fluid, such as blood cells, blood or urine, or blood transfusion, or a sample distributor which examines the quality of water in rivers, sewerage. A typical sample distributor of this type is provided with a probe capable of sucking and discharging a sample, and a syringe connected to the probe.

The portion extending from the pressure chamber of the syringe to the tip of the probe is filled with air as a pressure transmission medium. The pressuring/depressurizing action of the syringe will therefore act on the tip of the probe via air, so that a predetermined quantity of a sample (e.g., blood cells or urine) can be sucked or discharged from the tip of the probe.

Such a probe is cleaned with purging water in order to decontaminate an apparatus and eliminate a stuck sample.

In a test concerning blood transfusion, blood cells, blood plasma, blood serum or the like is used as a sample, and such samples of different physical properties are often tested at a time. In this respect, a conventional sample distributor uses two probes, which distribute blood cells and blood plasma or blood serum separately.

Sufficient sample purging has not however been done in the conventional sample distributing method, giving rise to a problem of infecting people with diseases, such as virus hepatitis and acquired immunodeficiency, through the samples remaining on or in the probes. The probes may be purged over a long period of time, which however requires a vast amount of purging water and is not so effective.

In addition, the conventional sample distributing method is designed on the premise that a sample is blood serum with low viscosity, relatively clean sewerage, or the like. In distributing samples with high viscosity which contain a surfactant such as blood cells or protein, therefore, air serves as a cushion against the distributing pressure, so that the quantity of the distributed sample will not be steady.

Further, the conventional sample distributing method hardly considers mutual contamination of sucked samples. In other words, in a clinical scientific test which has been the main flow of the conventional blood test, the difference between the lowest value and the highest value of each test item is about 100 fold. In a test of infectious diseases people are recently paying attention, to the difference between the lowest and highest values is approximately 100,000 to 1,000,000 fold. When this type of test is conducted by the conventional clinical scientific testing method, the number of false positive decisions would conspicuously increase due to the mutual contamination between samples.

Furthermore, as the number of probes is determined in accordance with samples with different physical properties in tests involving blood transfusion, the testing apparatus becomes inevitably large and the sample distributing method becomes complex, besides the considerable increase in false positive decisions in the tests of infectious diseases due to the mutual contamination between samples.

SUMMARY OF THE INVENTION

It is therefore an object of the present invention to provide a sample distributing method which does not have the above shortcomings and which has a probe that is designed to be detachable to prevent infection and contamination, and can control the quantity of a sample to be distributed at high precision.

To achieve this object, a sample distributing method according to the present invention is designed to use extruding water as a pressure transmission medium, and have an air layer formed above a sample sucked into a probe.

Accordingly, the sample distributing method of this invention can prevent contamination between samples and control the extruding quantity of a sample at high accuracy.

It is another object of the present invention to provide a sample distributing method which can distribute samples with different properties with one probe at a time and at high precision.

To achieve this object, a sample distributing method according to this invention is designed to alter the sucking speed and extruding speed in accordance with the property of a sample.

Accordingly, the sample distributing method of this invention can distribute samples with different properties with one probe at a time and at high precision.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

A sample distributing method according to the first embodiment of the present invention will now be described referring to FIGS. 1 and 2.

Figure 1:
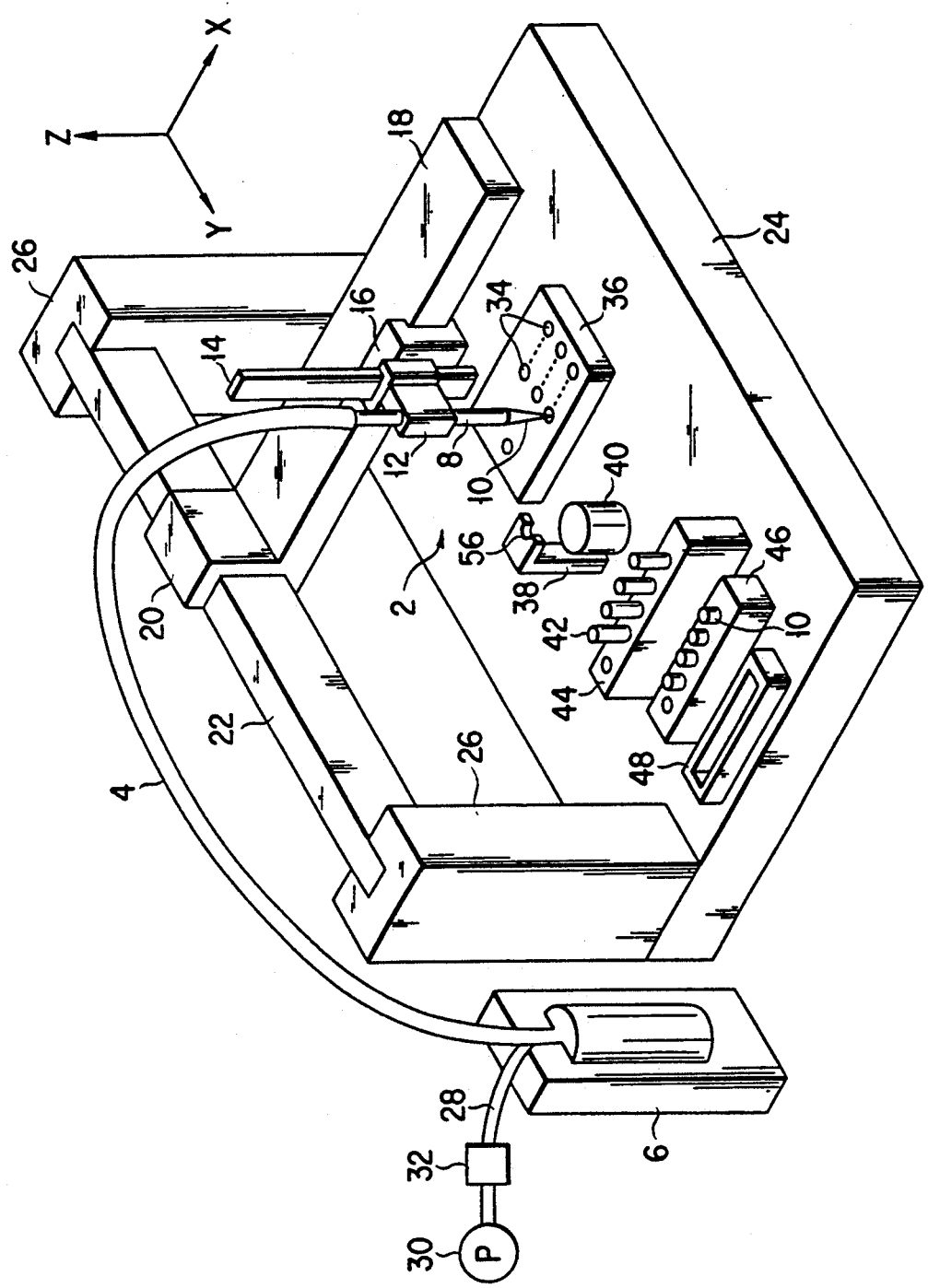
FIG. 1 is a schematic diagram illustrating the structure of a sample distributor adapted for a sample distributing method according to the first embodiment of the present invention.

FIG. 1 schematically illustrates the structure of a sample distributor adapted for a sample distributing method according to this embodiment.

As shown in FIG. 1, the sample distributor comprises a probe assembly 2, a connection tube 4 extending upward from this probe assembly 2, and a syringe 6 connected to the extending end of the connection tube 4. The probe assembly 2 has a chip 8 to which the connection tube 4 is connected, and a probe 10 detachably attached to the bottom of the chip 8.

The chip 8 of the probe assembly 2 is supported on a first support 12, which is engaged slidable with a first guide portion 14 extending in the direction of Z in the diagram.

The first guide portion 14 is supported on a second support 16, which is engaged slidable with a second guide portion 18 extending in the direction of X in the diagram. The second guide portion 18 has its proximal end 20 engaged slidable with a third guide portion 22, which extends in the direction of Y in the diagram. Both ends of the third guide portion 22 are held by a pair of holding members 26 extending in the Z direction from a base 24 of the sample distributor in FIG. 1.

The connection tube 4 couples a pressure chamber (not shown) of the syringe 6 to the probe assembly 2, and is designed to be able to fill non-compressive extruding water 7 (see FIG. 2), e.g., ion exchange water, into the pressure chamber of the syringe 6 and the probe assembly 2. The pressuring/depressurizing action of the syringe 6 therefore act directly on the tip portion of the probe 10 of the probe assembly 2 via the extruding water 7.

A filing tube 28, extending from the pressure chamber of the syringe 6, is connected with a pump 30 for filling the extruding water 7 and a solenoid valve 32 for controlling the timing for pressurized feeding of the extruding water 7 pumped out from the pump 30.

The base 24 is provided with a reaction container 36 having a plurality of reaction cells 34, and a separator 38 for separating the probe 10 from the chip 8. The probe 10 separated by the separator 38 falls into a retainer 40 located at the bottom portion of the separator 38. The base 24 is also provided with a container rack 44 capable of receiving a plurality of sample containers 42 containing predetermined samples, probe rack 46 retaining a plurality of unused probes 10, and a drainer 48.

The operation of the thus constituted sample distributor will be described below referring to FIGS. 1 and 2.

First, a drive section (not shown) is activated to move the second guide portion 18 in the Y direction (toward the probe rack 46). When the chip 8 with no probe 10 mounted thereon is positioned above the probe rack 46, the drive section is activated to move the second support 16 in the X direction (in the lengthwise direction of the probe rack 46). When the lower end portion of the chip 8 is aligned with the proximal end of a predetermined probe 10, the drive section is activated again to lower the first support 12 in the Z direction (in the direction to approach the probe 10).

When the chip 8 moves down and the outer periphery of the lower end of the chip 8 fitted on the inner periphery of the proximal end of the probe 10, the drive section is activated to lift the first support 12 in the Z direction (away from the probe rack 46), and then moves the second guide portion 18 in the Y direction (in the direction to approach the drainer 48). When the tip portion of the probe 10 is positioned above the drainer 48, the pump 30 and the solenoid valve 32 are activated. The extruding water 7 is then pumped into the pressure chamber (not shown) of the syringe 6 via the filing tube 28. At the same time, pressuring the syringe 6 will supply the extruding water 7 via the connection tube 4 into the probe 10 of the probe assembly 2.

The extruding water 7 supplied into the probe 10 spurts from the tip of the probe 10, dropping into the drainer 48. As a result, the bubbles in the connection tube 4 and the probe assembly 2 are removed.

Figure 2:
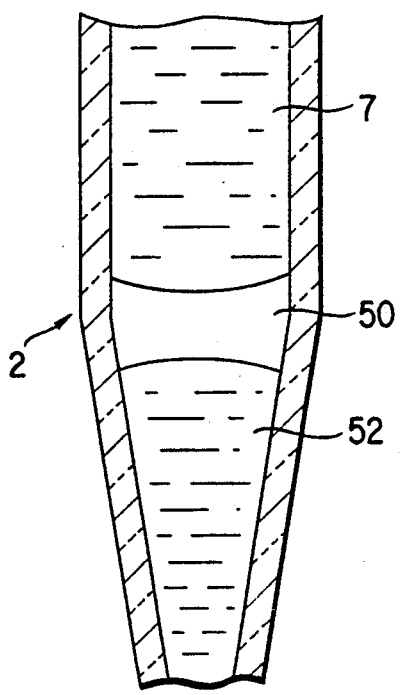
FIG. 2 illustrates a sample sucked via an air layer into a probe assembly of the sample distributor shown in FIG. 1.

Then, the syringe 6 is depressurized to suck a slight amount of air into the tip portion of the probe 10 to form an air layer 50 (see FIG. 2). Next, the drive section is activated to move the second guide portion 18 in the Y direction (toward the container rack 44). When the tip portion of the probe 10 is positioned above the container rack 44, the drive section is activated to move the second support 16 in the X direction (the lengthwise direction of the container rack 44).

When the tip portion of the probe 10 is aligned with the opening of a predetermined sample container 42, the drive section is activated to gently lower the first support 12 in the Z direction (toward the sample container 42). Consequently, the tip portion of the probe 10 is inserted into the sample container 42 through that opening. After the inserted tip portion of the probe 10 contacts the surface of a sample 52 (see FIG. 2) retained in the sample container 42, that tip portion is further dipped by a predetermined amount into the sample 52.

Whether or not the tip portion of the probe 10 contacts the sample 52 may be detected electrically or may be confirmed by a method of measuring the amount of the sample in advance using some optical method or ultrasonic, and then storing that value in a memory. In this manner, it is possible to control the insertion of the probe 10 so that the probe 10 will not be over-dipped in the sample 52.

When the tip portion of the probe 10 is put inside the sample 52 by a predetermined amount, the syringe 6 is depressurized to suck the sample 52 into the probe 10 (see FIG. 2).

After the suction of the sample 52, the drive section is activated again to lift the first support 12 in the Z direction (away from the container rack 44). At the same time, the second guide portion 18 is moved in the Y direction (toward the reaction container 36).

When the tip portion of the probe 10 is positioned above the reaction container 36, the drive section is activated to move the second support 16 in the X direction (lengthwise direction of the reaction container 36). When the tip portion of the probe 10 is positioned above a predetermined reaction cell 34, the drive section is activated to lower the first support 12 in the Z direction (toward the reaction cell 34). When the distance between the tip portion of the probe 10 and the inner wall of the reaction cell 34 becomes the optimal distance, the first support 12 stops the downward movement.

At this time, the syringe 6 is pressurized to push out the extruding water 7 toward the probe assembly 2. This pressure presses the air layer 50 formed in the probe 10 to compress the air layer 50. The repulsion against this compression pushes the sample 52 sucked in the tip portion of the probe 10 toward the tip of the probe 10. Consequently, the sample 52 is discharged from the probe 10 into the reaction cell 34.

As described above, the pressuring action of the syringe 6 can directly act on the tip portion of the probe 10 through the non-compressive extruding water 7. The delicate action of the syringe 6 can therefore act on the sample 52 sucked into the tip portion of the probe 10 at high precision. The discharging quantity of the sample 52 can therefore be controlled at very high accuracy by controlling the pressuring operation of the syringe 6 in accordance with the desired quantity of the sample 52 to be discharged.

The provision of the air layer 50 (see FIG. 2) in the probe 10 can prevent the extruding water 7 (see FIG. 2), upon sample discharge, from being mixed into the sample 52 to be discharged. In other words, since the air layer 50 is provided below the extruding water 7, the extruding water 7 is shielded by this air layer 50, thereby preventing the extruding water 7 from being mixed into the to-be-discharged sample 52 sucked into the tip portion of the probe 10.

According to the sample distributing method of this embodiment, because the air layer 50 serves as a stopper to the extruding water 7, the extruding water 7 will not pass over the air layer 50 to be mixed into the sample 52 sucked into the tip portion of the probe 10, even in the case where the sample 52 has high viscosity and contains a component having an surface active effect such as protein. Accordingly, this sample distributing method can distribute a sample 52 with any property at high precision.

After the discharge of the sample 52 is completed, the drive section is activated to lift the first support 12 in the Z direction (away from the reaction container 36). Then, the second guide portion 18 is moved in the Y direction (toward the separator 38). When the probe assembly 2 is positioned above the separator 38, the drive section is activated to move the second support 16 in the X direction (in the direction for the probe 10 to be aligned with a recess 56 of the separator 38). When the tip portion of the probe 10 is aligned with the recess 56 of the separator 38, the drive section is activated to lower the first support 12 in the Z direction (toward the recess 56). When the probe 10 is engaged with the recess 56, the first support 12 is gently lifted upward in the Z direction (away from the recess 56). As a result, the probe 10 is detached from the chip 8 while kept engaged with the recess 56. The detached probe 10 is dropped into the retainer 40 located at the bottom portion of the separator 38.

Disposing the used probe 10 in this manner can prevent infection by an infectious sample 52. It is preferable that a drag having a germicidal action be retained in advance in the retainer 40. This will also prevent air infection by the help of such a drag. The probe 10 may be used again in this case.

The chip 8 from which the probe 10 has been separated is set at the initial position for the suction/discharge of the next sample.

The sample distributing method according to this invention is not limited to the particular design of the above-described embodiment. For instance, a removal step of removing a sample stuck on the outer wall of the probe 10 may be added after the suction of the sample 52. This step will improve the accuracy of distributing the sample 52.

A sample distributing method according to the second embodiment of the present invention will now be explained referring to FIGS. 1 and 3. In the following description, like or same reference numerals are used to denote components which are like or identical to those of the first embodiment to avoid their otherwise redundant description.

In the sample distributing method according to this embodiment, the steps up to the suction of a sample 52 into the probe 10 mounted on the chip 8 are the same as those discussed in the foregoing description of the first embodiment, so that the description of those steps will not be given below.

In the sample distributing method according to this embodiment, the first sample 52 sucked serves to prevent the extruding water 7 (see FIG. 3) from being mixed into a sample 52 to be discharged at the time of discharge of the latter sample 52, which will be described later. In this respect, the first sample sucked will be called "supplemental sample 52a" (see FIG. 3) to clearly distinguish it from the target sample 52 to be discharged.

After a predetermined amount of a supplemental sample 52a is sucked into the probe 10, the drive section is activated to gently lift the first support 12 in the Z direction (away from the container rack 44). When the tip portion of the probe 10 is moved away from the surface of the sample 52, the syringe 6 is depressurized to suck a slight amount of air into the tip portion of the probe 10 to form another air layer 60 (see FIG. 3). Then, the first support 12 is gently lowered again in the Z direction (toward the sample 52 in the sample container 42).

Figure 3:
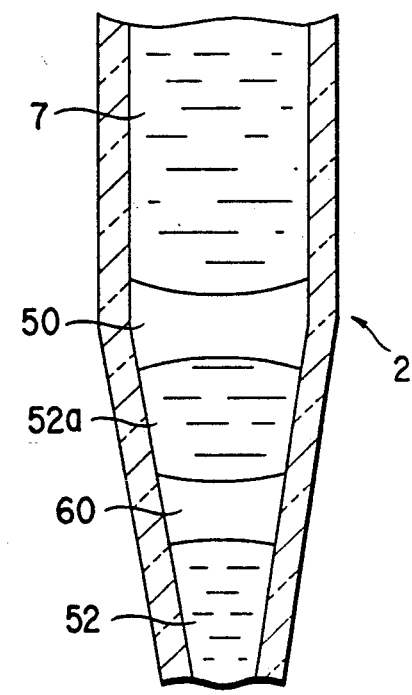
FIG. 3 is a diagram showing a supplemental sample and a sample with an air layer therebetween, both sucked into a probe assembly of a sample distributor adapted for a sample distributing method according to the second embodiment of the present invention.

When the tip portion of the probe 10 is put inside the sample 52 by a predetermined amount, the syringe 6 is depressurized to suck a predetermined quantity of the sample 52 into the probe 10 (see FIG. 3).

The sample 52 sucked at this time is the same sample as the supplemental sample 52a, and is the target sample 52 to be discharged into the reaction cell 34 at the time of sample discharge to be described later.

After the suction of the sample 52, the drive section is activated to lift the first support 12 in the Z direction (away from the container rack 44). At the same time, the second guide portion 18 is moved in the Y direction (toward the reaction container 36). When the tip portion of the probe 10 is positioned above the reaction container 36, the drive section is activated to move the second support 16 in the X direction (lengthwise direction of the reaction container 36).

When the tip portion of the probe 10 is positioned above a predetermined reaction cell 34, the drive section is activated to lower the first support 12 in the Z direction (toward the reaction cell 34). When the distance between the tip portion of the probe 10 and the inner wall of the reaction cell 34 becomes the optimal distance, the first support 12 stops the downward movement. At this time, the syringe 6 is pressurized to push out the extruding water 7 toward the probe assembly 2. This pressure presses the air layer 50 formed in the probe 10 to compress the air layer 50. The repulsion against this compression acts on the supplemental sample 52a to push the sample 52a. The repulsion against this pushing action acts on the additional air layer 60 to compress the air layer 60. The repulsion against this compression pushes the sample 52 sucked in the tip portion of the probe 10 toward the tip of the probe 10. Consequently, the sample 52 is discharged from the probe 10 into the reaction cell 34.

As described above, the pressuring action of the syringe 6 can directly act on the tip portion of the probe 10 through the non-compressive extruding water 7. The delicate action of the syringe 6 can therefore act on the sample 52 sucked into the tip portion of the probe 10 at high precision. The discharging quantity of the sample 52 can therefore be controlled at very high accuracy by controlling the pressuring operation of the syringe 6 in accordance with the desired quantity of the sample 52 to be discharged into the reaction cell 34.

The provision of two air layers 50 and 60 (see FIG. 3) in the probe 10 can prevent the extruding water 7 (see FIG. 3), upon sample discharge, from being mixed into the sample 52 to be extruded. In other words, even if the extruding water 7 penetrates through the gap between the upper air layer 50 and the inner wall of the probe 10 to be mixed into the supplemental sample 52a, the underlying second air layer 60 will shield the extruding water 7. The extruding water 7 can therefore be prevented from being mixed into the target sample 52 sucked into the tip portion of the probe 10.

According to the sample distributing method of this embodiment, because the two air layers 50 and 60 serve as a double stopper to the extruding water 7, the extruding water 7 will not penetrate through both air layers 50 and 60 to be mixed into the sample 52, sucked into the tip portion of the probe 10, even in the case where the sample 52 has high viscosity and contains a component having an surface active effect such as protein. Accordingly, this sample distributing method can distribute a sample 52 with any property at high precision.

In this embodiment like in the first embodiment, after the discharge of the sample 52 is completed, the probe 10 is detached from the chip 8 by the separator 38, dropping into the retainer 40.

Disposing the used probe 10 in this manner can prevent infection by an infectious sample 52. It is preferable that a drag having a germicidal action be retained in advance in the retainer 40. This will also prevent air infection by the help of such a drag. The probe 10 may be used again in this case.

The chip 8 from which the probe 10 has been separated is set at the initial position for the suction/extrusion of the next sample.

The sample distributing method according to this invention is not limited to the particular design of the above-described second embodiment. For instance, a removal step of removing a sample stuck on the outer wall of the probe 10 may be added after the suction of the sample 52. This step will improve the accuracy of distributing the sample 52. In addition, only the second air layer 60 may be provided in the probe 10, in which case it is desirable that a relatively large quantity of a sample 52 is sucked into the probe 10 so that the extruding water 7, even when penetrating through the air layer 60 to be mixed into the sample 52 at the time of sample extrusion, will not affect the discharging quantity of the target sample 52.

A sample distributing method according to the third embodiment of the present invention will now be explained referring to FIGS. 1 and 4. In the following description, like or same reference numerals are used to denote components which are like or identical to those of the above-described embodiments to avoid their otherwise redundant description.

The feature of the sample distributing method of this embodiment lies in simultaneous distribution of samples with different properties in a single probe.

In the sample distributing method according to this embodiment, the steps up to the depressurizing of the syringe 6 to suck a slight amount of air into the tip portion of the probe 10 to form the air layer 50 are the same as those discussed in the foregoing description of the individual embodiments, so that the description of those steps will not be given below.

Samples used in the sample distributing method of this embodiment are what is acquired by subjecting coagulant-containing blood to centrifugal separation or the like to be separated into blood plasma and blood cells (the blood plasma located above the blood cells).

After the air layer 50 (see FIG. 4) is formed, the drive section is activated to move the second guide portion 18 in the Y direction (toward the container rack 44). When the tip portion of the probe 10 is positioned above the container rack 44, the drive section is activated to move the second support 16 in the X direction (the lengthwise direction of the container rack 44).

When the tip portion of the probe 10 is aligned with the opening of a predetermined sample container 42, the drive section is activated to gently lower the first support 12 in the Z direction (toward the sample container 42). Consequently, the tip portion of the probe 10 is inserted into the sample container 42 through that opening. After the inserted tip portion of the probe 10 contacts the surface of a sample or blood plasma 52 (see FIG. 4) retained in the sample container 42, that tip portion is further dipped by a predetermined amount into the blood plasma 52.

Whether or not the tip portion of the probe 10 contacts the blood plasma 52 may be detected electrically or may be confirmed by a method of measuring the amount of the blood plasma in advance using some optical method or utrasonic, and then storing that value in a memory. This process is executed for the purpose of preventing erroneous suction of blood cells at the time of sucking the blood plasma 52.

Figure 4:
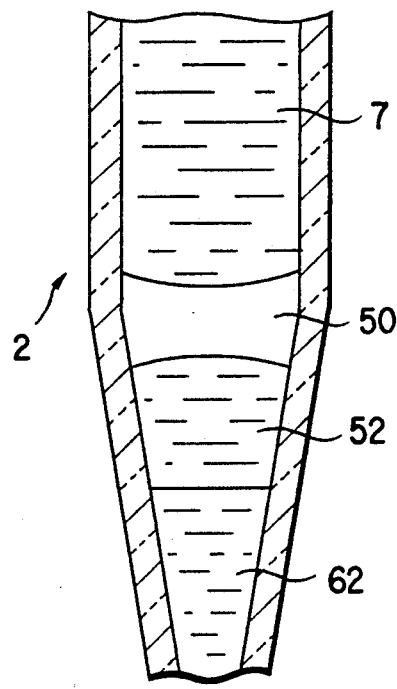
FIG. 4 is a diagram showing a sample with different properties sucked via an air layer into a probe assembly of a sample distributor adapted for a sample distributing method according to the third embodiment of the present invention.

After the tip portion of the probe 10 is dipped into the blood plasma 52, a pulse with a relatively high pulse rate (e.g., 1,500 PPS) is transmitted to the syringe 6 from a pulse generator (not shown) to depressurize the syringe 6, permitting suction of a predetermined amount of the blood plasma 52 into the probe 10 (see FIG. 4). In sucking such blood plasma 52 or blood serum (not shown) having low viscosity, applying a pulse with a relatively high pulse rate to the syringe 6 can accomplish efficient suction of the blood plasma 52 or blood serum.

After the suction of the blood plasma 52, the drive section is activated to further lower the first support 12 in the Z direction (toward the container rack 44) gently, causing the tip portion of the probe 10 to be dipped into the blood cells 62 (see FIG. 4).

The suction of the blood plasma 52 and blood cells 62 may be accomplished by sucking a target sample after detecting the interface between the blood plasma and the blood cells in the sample container 42, or sucking the blood cells 62 first after lowering the tip portion of the probe 10 close to the bottom of the sample container 42.

In the suction of the blood cells 62, it is preferable that a pulse with a relatively low pulse rate (e.g., 800 PPS) is applied to the syringe 6 to permit the suction of a predetermined amount of the blood cells 62 into the probe 10 (see FIG. 4).

This is because in sucking such blood cells 62 having high viscosity, applying a pulse with a relatively low pulse rate to the syringe 6 can accomplish suction of the blood cells 62 at a sufficiently high accuracy.

Upon suction of the blood plasma 52 and blood cells 62, the drive section is activated to move the first support 12 in the Z direction (away from the container rack 44), and move the second guide portion 18 in the Y direction (toward the reaction container 36) at the same time. When the tip portion of the probe 10 is positioned above the reaction container 36, the drive section is activated to move the second support 16 in the X direction (lengthwise direction of the reaction container 36). When the tip portion of the probe 10 is positioned above a predetermined reaction cell 34, the drive section is activated to lower the first support 12 in the Z direction (toward the reaction cell 34). When the distance between the tip portion of the probe 10 and the inner wall of the reaction cell 34 becomes the optimal distance, the first support 12 stops the downward movement.

At this time, a pulse with a given pulse rate is applied to the syringe 6 from the pulse generator (not shown) to pressurize the syringe 6, thus pushing out the extruding water 7 toward the probe assembly 2. This pressure presses the air layer 50 formed in the probe 10 to compress the air layer 50. The repulsion against this compression pushes the blood plasma 52 and blood cells 62, sucked in the tip portion of the probe 10, toward the tip of the probe 10. This pressing action discharges the blood cells 62 first from the probe 10 into the reaction cell 34.

The pulse rate in this discharge may be the same as the one used at the time of the suction of the blood cells 62, but may be altered as needed. More specifically, in discharging the blood cells 62 with high viscosity, only the proper amount of the blood cells 62 can be discharged sufficiently by the application of a pulse with a relative low pulse rate.

After the discharge of the blood cells 62 is completed, a pulse with a given pulse rate is applied to the syringe 6 from the pulse generator (not shown) to pressurize the syringe 6, thus pushing out the extruding water 7 toward the probe assembly 2. This pressure presses the air layer 50 formed in the probe 10 to compress the air layer 50. The repulsion against this compression pushes the blood plasma 52, having moved to the tip portion of the probe 10 by now, toward the tip of the probe 10. This pressing action discharges the blood plasma 52 first from the probe 10 into the reaction cell 34.

The pulse rate in this extrusion may be the same as the one used at the time of the suction of the blood cells 62, but may be altered as needed. More specifically, in extruding the blood plasma 52 or blood serum (not shown) with low viscosity, the blood plasma 52 or blood serum can be extruded efficiently by the application of a pulse with a relative high pulse rate.

In this embodiment like in the above-described individual embodiments, after the discharging step is completed, the probe 10 is detached from the chip 8 by the separator 38, dropping into the retainer 40.

Disposing the used probe 10 in this manner can prevent infection by an infectious sample 52. It is preferable that a drag having a germicidal action be retained in advance in the retainer 40. This will also prevent air infection by the help of such a drag. The probe 10 may be used again in this case.

The chip 8 from which the probe 10 has been separated is set at the initial position for the suction/extrusion of the next sample.

The sample distributing method according to this embodiment can simultaneously allow the blood plasma 52 and blood cells 62 or blood serum (not shown), which have different properties, to be distributed into a single probe at high accuracy.

The sample distributing method according to this invention is not limited to the particular design of the above-described third embodiment. For instance, a removal step of removing blood plasma 52 and blood cells 62 stuck on the outer wall of the probe 10 may be added after the suction of the blood plasma 52 and blood cells 62. This step will improve the sample distributing accuracy. Further, an air layer may be provided between the blood plasma 52 and blood cells 62 in the probe 10. The provision of such an air layer can separate the blood plasma 52 and blood cells 62, sucked into the probe 10, from each other, thereby preventing mixture of the blood plasma 52 and blood cells 62. When the air layer is formed, a dummy discharging step is needed in the sample discharging step to remove the air layer.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A sample distributing method comprising the steps of:
   mounting a probe having an open tip portion on a mounting member;
   sucking a predetermined sample into said probe through said open tip portion thereof;
   discharging said sample from said probe through said open tip portion thereof to a discharging position;
   detaching said probe from said mounting member; and
   introducing, before said sucking step, an effective amount of a pressure transmission liquid into said probe and retaining said pressure transmission liquid in said probe so that a quantity of air is removed from an interior portion of said probe, and wherein:
   said sucking step comprises sucking each of a plurality of different samples, each having a different known viscosity, separately into said probe;
   said sucking step and said discharging steps are respectively controlled by applying different pressures to said pressure transmission liquid, based on the viscosity of each of said plurality of different samples; and
   said discharging step comprises separately discharging each of said plurality of different samples from said probe.

2. A sample distributing method according to claim 1, wherein said introducing step further comprises filling said probe with said pressure transmission liquid.

3. A sample distributing method according to claim 2, wherein said filling step comprises flowing an amount of said pressure transmission liquid out of said open tip portion of said probe.

4. A sample distributing method according to claim 3, wherein said introducing step further comprises positioning said probe above a drainer and flowing said amount of said pressure transmission liquid into said drainer.

5. A sample distributing method according to claim 1, wherein, during said sucking step, said plurality of different samples are successively sucked into said probe.

* * * * *